United States Patent [19]

Fürstenwerth et al.

[11] Patent Number: 5,328,993
[45] Date of Patent: Jul. 12, 1994

[54] CATIONIC TRIAZATRIMETHINE DYESTUFFS

[75] Inventors: Hauke Fürstenwerth, Leverkusen; Karl-Heinrich Lange, Burscheid; Roderich Raue, Leverkusen; Alfred Brack, Odenthal, all of Fed. Rep. of Germany

[73] Assignee: Bayer Aktiengesellschaft, Leverkusen, Fed. Rep. of Germany

[21] Appl. No.: 47,327

[22] Filed: Apr. 15, 1993

[30] Foreign Application Priority Data

Dec. 15, 1992 [DE] Fed. Rep. of Germany ....... 4242429

[51] Int. Cl.$^5$ .................. C09B 26/06; D06P 1/41; D06P 3/76; C08K 5/46
[52] U.S. Cl. .................. 534/551; 534/555; 8/638; 8/644; 8/655; 8/927; 8/922; 8/924; 524/83; 524/190
[58] Field of Search .................. 534/551; 524/83, 190; 8/638, 644, 655, 928

[56] References Cited

U.S. PATENT DOCUMENTS

| | | | |
|---|---|---|---|
| 2,978,290 | 4/1961 | Bossard et al. | 534/551 X |
| 4,268,438 | 5/1981 | Furstenwerth | 534/607 |
| 4,382,801 | 5/1983 | Loew | 534/551 X |
| 4,432,897 | 2/1984 | Furstenwerth | 534/551 |
| 4,500,715 | 2/1985 | Furstenwerth | 548/140 |

FOREIGN PATENT DOCUMENTS

| | | |
|---|---|---|
| 572834 | 10/1959 | Belgium . |
| 0053751 | 11/1981 | European Pat. Off. . |
| 0446731 | 3/1991 | European Pat. Off. . |
| 1069563 | 11/1959 | Fed. Rep. of Germany . |
| 49-27332 | 7/1974 | Japan .................. 534/551 |
| 884582 | 12/1961 | United Kingdom . |
| 2017134 | 3/1979 | United Kingdom . |

OTHER PUBLICATIONS

Balli et al., Liebigs Ann. Chem. 663, 103-107 (1963).
Miyahara et al., Chem. Pharm. Bull., 30(12) 4402-4406 (1982).

*Primary Examiner*—Mary C. Lee
*Assistant Examiner*—Fiona T. Powers
*Attorney, Agent, or Firm*—Sprung Horn Kramer & Woods

[57] ABSTRACT

The new cationic triazatrimethine dyestuffs of the formula

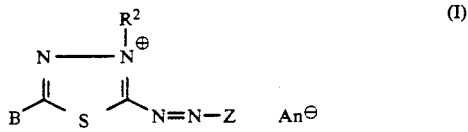

wherein the substituents B, Z, R$^2$ and An$^\ominus$ have the meaning given in the description, are suitable for dyeing and printing naturally occurring and synthetic materials.

12 Claims, No Drawings

CATIONIC TRIAZATRIMETHINE DYESTUFFS

The present invention relates to new cationic triazatrimethine dyestuffs, processes for their preparation and their use for dyeing and printing naturally occurring and synthetic materials, in particular fibres of polyacrylonitrile and acid-modified polyesters and polyamides.

The new triazatrimethine dyestuffs correspond to the general formula (I)

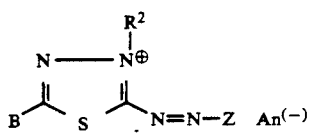

wherein
Z represents a radical of the formula

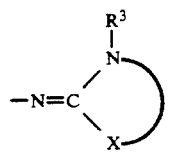

wherein
$R^3$ represents hydrogen or an alkyl, alkenyl or aralkyl radical and
X represents the remaining members of a five-membered, optionally substituted and optionally fused partly unsaturated heterocyclic ring which contains one to three hetero atoms selected from the group consisting of oxygen, sulphur and nitrogen,
B represents alkylmercapto, arylmercapto or a radical of the formula

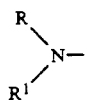

wherein
R denotes hydrogen or an alkyl, alkenyl, acyl, cycloalkyl, aryl, aralkyl, amino, alkylamino, dialkylamino, arylamino, aralkylamino or heterocyclic radical and
$R^1$ denotes hydrogen or an alkyl, alkenyl or aralkyl radical, or
R and $R^1$ together with the nitrogen atom to which they are attached form a heterocyclic ring,
$R_2$ represents hydrogen or an alkyl, alkenyl, alkinyl or aralkyl radical and
$An^{(-)}$ represents an anion,
and wherein the cyclic and acyclic radicals can contain non-ionic substituents and/or a carboxyl group.

Non-ionic substituents in the context of the present invention are the non-dissociating substituents customary in dyestuff chemistry, such as, for example, cyano, hydroxyl, halogen, such as fluorine, chlorine or bromine, nitro, alkyl, mono- and dialkylamino, phenyl, alkoxy, acyloxy, alkoxycarbonyl and alkoxycarbonyloxy, alkyl and alkoxy preferably containing 1 to 4 C atoms and acyl representing, in particular, $C_1$–$C_4$-alkylcarbonyl.

Alkyl radicals in the context of this invention, including those in composite terms, such as alkylamino, are, for example, those having 1 to 8, in particular 1 to 4, C atoms.

Substituents of the alkyl radicals $R^1$, $R^2$ and $R^3$ are, for example, halogen, hydroxyl, $C_1$–$C_4$-alkoxy, phenyloxy, benzyloxy, $C_1$–$C_4$-alkoxycarbonyl, carboxyl, amidocarbonyl or cyano, and halogen preferably represents fluorine, chlorine and bromine. Alkenyl and alkinyl radicals are understood as meaning, in particular, those having 2 to 5 C atoms.

Cycloalkyl represents, for example, cyclopentyl or cyclohexyl which is optionally substituted by $C_1$–$C_4$-alkyl. Suitable acyl radicals are, for example, $C_1$–$C_3$-alkylcarbonyl, benzoyl which is optionally substituted by halogen or $C_1$–$C_4$-alkyl, $C_1$–$C_4$-alkoxycarbonyl, mono- and di-$C_1$–$C_4$-alkylaminocarbonyl, benzylaminocarbonyl, $C_1$–$C_4$-alkylsulphonyl, phenylsulphonyl or di-$C_1$–$C_4$-alkylaminosulphonyl.

Aryl is understood as meaning, in general, phenyl or naphthyl, and aralkyl is understood as meaning benzyl and $\beta$-phenyl-$C_2$–$C_4$-alkyl. The phenyl radicals can be substituted by, for example, 1 to 3 non-ionic radicals, such as halogen, $C_1$–$C_4$-alkyl, $C_1$–$C_4$-alkoxy, $C_1$'$C_4$-alkoxycarbonyl, carboxyl, amidocarbonyl, cyano, nitro, amidosulphonyl, $C_1$–$C_3$-alkylcarbonylamino, benzoylamino, hetaryl or arylazo. Hetaryl is understood here as meaning, for example, benzothiazolyl which is optionally substituted by $C_1$–$C_4$-alkyl or $C_1$–$C_4$-alkoxy.

The radicals R and $R^1$, together with the nitrogen atom to which they are bonded, can preferably form a 5- or 6-membered ring, such as pyrrolidine, piperidine, morpholine, piperazine or N-methyl- or N-hydroxyethylpiperazine.

Possible anionic radicals are the organic and inorganic anions customary for cationic dyestuffs.

Colourless anions are preferred. The anion is in general determined by the preparation process and any purification carried out on the crude dyestuff. The dyestuffs are in general present in the form of halides (in particular in the form of chlorides or bromides) or in the form of methosulphates, ethosulphates, sulphates or benzene- or toluenesulphonates, or in the form of acetates. The anions can be replaced by other anions in a known manner.

Preferred triazatrimethine dyestuffs of the formula (I) are those wherein
Z represents a radical of the formula

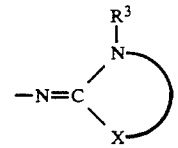

wherein
$R^3$ represents hydrogen, $C_1$–$C_8$-alkyl, which is optionally substituted by hydroxyl, halogen, cyano, $C_1$–$C_4$-alkoxy, carboxyl, $C_1$–$C_4$-(di)-alkylamino, $C_1$–$C_4$-alkoxycarbonyl or $C_1$–$C_4$-alkylsulphonyl, or represents $C_2$–$C_4$-alkenyl, or represents phenyl-$C_1$–$C_2$-alkyl, which is optionally substituted by halogen, cyano, $C_1$–$C_4$-alkyl or $C_1$–$C_4$-alkoxy and
X represents the remaining members of a thiazoline, isothiazoline, benzothiazoline, 1,2,4-triazoline, 1,3,4-thiadiazoline, oxazoline, benzoxazoline, imidazoline, benzimidazoline, pyrazoline or benzopyrazoline ring, which is in each case optionally mono- or disubstituted by identical or different $C_1$-$C_8$-alkyl, which is optionally substituted by hydroxyl, halogen, cyano, $C_1$-$C_4$-alkoxy, carboxyl, $C_1$-$C_4$-(di)alkylamino, $C_1$-$C_4$-alkoxycarbonyl or $C_1$-$C_4$-alkylsulphonyl, or represents $C_2$-$C_4$-alkenyl, or represents phenyl-$C_1$-$C_2$-alkyl, which is optionally substituted by halogen, cyano, $C_1$-$C_4$-alkyl or $C_1$-$C_4$-alkoxy, B represents a radical of the formula

wherein

R represents hydrogen, a $C_1$-$C_8$-alkyl radical which is optionally substituted by hydroxyl, halogen, cyano, $C_1$-$C_4$-alkoxy, carboxyl, aminocarbonyl or $C_1$-$C_4$-alkoxycarbonyl, a $C_2$-$C_4$-alkenyl radical, a cyclohexyl radical which is optionally substituted by $C_1$-$C_4$-alkyl, a phenyl, benzyl or phenylethyl radical which is optionally substituted by halogen, $C_1$-$C_4$-alkyl or $C_1$-$C_4$-alkoxy, a $C_1$-$C_4$-alkyloxycarbonyl, mono- or di-$C_1$-$C_4$-alkylaminocarbonyl, aminocarbonyl, mono- or di-$C_1$-$C_4$-alkylaminosulphonyl, amino, $C_1$-$C_4$-alkylamino or $C_1$-$C_4$-dialkylamino radical, or represents a phenylamino or benzylamino radical which in each case is optionally substituted by $C_1$-$C_4$-alkyl or $C_1$-$C_4$-alkoxy and $R^1$ represents hydrogen, a $C_1$-$C_8$-alkyl radical which is optionally substituted by hydroxyl, halogen, cyano, $C_1$-$C_4$-alkoxy, carboxyl, aminocarbonyl or $C_1$-$C_4$-alkoxycarbonyl, a $C_2$-$C_4$-alkenyl radical or represents a phenyl, benzyl or phenylethyl radical which in each case is optionally substituted by halogen, $C_1$-$C_4$-alkyl or $C_1$-$C_4$-alkoxy, and $R^2$ represents hydrogen, a $C_1$-$C_8$-alkyl radical which is optionally substituted by hydroxyl, halogen, cyano, $C_1$-$C_4$-alkoxy, carboxyl, aminocarbonyl or $C_1$-$C_4$-alkoxycarbonyl, a $C_2$-$C_4$-alkenyl radical or represents benzyl or phenylethyl radical which in each case is optionally substituted by halogen, $C_1$-$C_4$-alkyl or $C_1$-$C_4$-alkoxy.

Particularly preferred dyestuffs of the formula (I) are those wherein

Z represents a radical of the formula

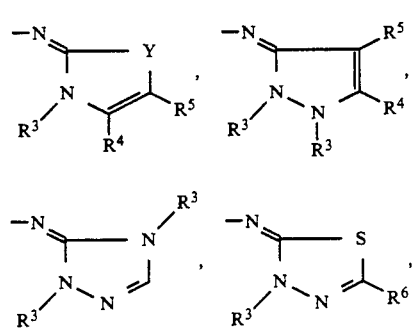

or

-continued

wherein

Y represents —S—, —O— or

wherein $R^3$ has the abovementioned meaning, and if two substituents $R^3$ occur, these can be identical or different, $R^4$ and $R^5$ either represent hydrogen, or together represent the remaining members of a fused-on benzene ring, and $R^6$ represents $C_1$-$C_4$-(di)alkylamino, $C_6$-$C_{10}$-(di)arylamino, piperazino, pyrrolidino, $C_1$-$C_4$-alkylmercapto or $C_6$-$C_{10}$-arylmercapto, B represents a radical of the formula

wherein

R represents hydrogen, a $C_1$-$C_4$-alkyl radical which is optionally substituted by hydroxyl, halogen, cyano, $C_1$-$C_4$-alkoxy, carbonyl, aminocarbonyl or $C_1$-$C_4$-alkoxycarbonyl, or represents a phenyl, benzyl or phenylethyl radical which in each case is optionally substituted by halogen, $C_1$-$C_4$-alkyl or $C_1$-$C_4$-alkoxy and $R^1$ represents a $C_1$-$C_4$-alkyl radical which is optionally substituted by hydroxyl, halogen, cyano, $C_1$-$C_4$-alkoxy, carboxyl, aminocarbonyl or $C_1$-$C_4$-alkoxycarbonyl, or represents a benzyl or phenylethyl radical which in each case is optionally substituted by halogen, $C_1$-$C_4$-alkyl or $C_1$-$C_4$-alkoxy, and $R^2$ represents hydrogen, a $C_1$-$C_8$-alkyl radical which is optionally substituted by hydroxyl, halogen, cyano, $C_1$-$C_4$-alkoxy, carboxyl, aminocarbonyl or $C_1$-$C_4$-alkoxycarbonyl or represents a benzyl or phenylethyl radical which in each case is optionally substituted by halogen, $C_1$-$C_4$-alkyl or $C_1$-$C_4$-alkoxy.

In the definition of $R^3$, $R^6$ and X $C_1$-$C_4$-(di)alkylamino means $C_1$-$C_4$-alkylamino and $C_1$-$C_4$-dialkylamino. In the definition of $R^6$ $C_6$-$C_{10}$-(di)-arylamino means $C_6$-$C_{10}$-arylamino and $C_6$-$C_{10}$-diarylamino.

The new triazatrimethine dyestuffs of the formula (I) can be prepared in a known manner by reaction of colour bases of the formula (II)

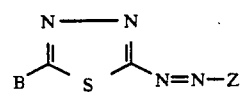

(II)

wherein

B and Z have the abovementioned meanings, with an alkylating agent from the class comprising alkyl halides, Michael acceptors or epoxides, such as are also mentioned, for example, in DE-A 2 811 258 on page 34.

In the case where the substituent B in formula (II) does not cause much steric hindrance, quaternisation in the 4-position of the thiadiazole ring can also occur to a certain percentage, which is usually less than 10%, during the reaction with the quaternising agent.

The colour bases of the formula (II) are likewise new, and the present invention relates to them. The colour bases of the formula (II) are likewise dyestuffs, and the invention furthermore relates to the use thereof for dyeing fibres and fabrics of materials which can be dyed with non-ionic dyestuffs, for example polyesters, and for dyeing plastics, especially for bulk dyeing of plastics such as, for example, polystyrene, polycarbonate, polyamide or acrylonitrile/butadiene/styrene copolymers.

The colour bases of the formula (II) can be prepared in a manner which is known per se, for example by the process described in DE-A 1 069 563, by diazotisation of heterocyclic amines and coupling to quaternary salts of the same or different heterocyclic amines. The diazotisation is carried out with alkali metal nitrites in aqueous mineral acid solution or in an aqueous solution of an organic acid. The diazonium salt solution thus obtained is combined with the solution of the coupling component, and the product is isolated, for example by filtration, if appropriate after buffering.

Alternatively, the new dyestuffs of the formula (II) can be prepared by a new process, to which the present invention likewise relates. The new process for the preparation of dyestuffs of the formula (II) is characterised in that a compound of the formula (IV)

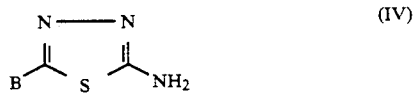
(IV)

wherein
B has the abovementioned meaning,
and a compound of the formula (V)

$H-Z^1$      (V)

wherein
$Z^1$ represents a radical of the formula

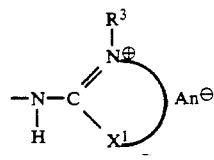

wherein
$R^3$ and $An^\ominus$ have the abovementioned meaning and
$X^1$ represents the remaining members of a quaternised five-membered optionally substituted and optionally fused, unsaturated heterocyclic ring which contains 1 to 3 hereto atoms selected from the group consisting of oxygen, sulphur and nitrogen, and preferably represents the remaining members of a quaternised thiazole, isothiazole, benzothiazole, 1,2,4-triazole, 1,3,4-thiadiazole, oxazole, benzoxazole, imidazole, benzimidazole, pyrazole or benzopyrazole ring, which is in each case optionally mono- or disubstituted by identical or different $C_1-C_8$-alkyl, which is optionally substituted by hydroxyl, halogen, cyano, $C_1-C_4$-alkoxy, carboxyl, $C_1-C_4$-(di)alkylamino, $C_1-C_4$-alkoxycarbonyl or $C_1-C_4$-alkylsulphonyl, or represents $C_2-C_4$-alkenyl, or represents phenyl-$C_1-C_4$-alkyl, which is optionally substituted by halogen, cyano, $C_1-C_4$-alkyl or $C_1-C_4$-alkoxy, are reacted in an aqueous medium with a substance which donates nitrous acid, in the presence of $CO_2$ under a pressure of 5 to 100 bar and at a temperature of 0° to 125° C. The reaction has in general ended after 10 minutes to 24 hours.

The process according to the invention is preferably carried out at a temperature from 0° to 100° C. particularly preferably from 0° to 70° C., and in particular from 30° to 40° C.

Water, if appropriate mixed with organic solvents which are completely or partly miscible with water, is suitable as the reaction medium.

Possible suitable solvents are methanol, ethanol, propanol, isopropanol, isoamyl alcohol, ethylene glycol, methylglycol, ethylglycol, butylglycol, ethylene glycol dimethyl ether, ethylene glycol diethyl ether, diethylene glycol dimethyl ether, glycol diacetate, methylglycol acetate, ethylglycol acetate, butylglycol acetate, propylene glycol, propylene glycol monomethyl ether, propylene glycol monoethyl ether, propylene glycol dimethyl ether, propylene glycol diethyl ether, propylene glycol acetate, triacetin, acetonitrile, tetrahydrofuran, dioxane, dimethylformamide and N-methyl-pyrrolidone.

It is preferable to use water or a mixture of water and methanol which has a ratio of water to methanol of preferably 1:0.2 to 1:10, particularly preferably 1:1 to 1:5 and in particular 1:2.

No reaction with $CO_2$ takes place under normal pressure. The reaction is preferably carried out under a pressure of 25 to 65 bar.

Inorganic and organic nitrites are particularly suitable substances donating nitrous acid.

Preferred inorganic nitrites are the nitrous acid salts of elements of the first, second and third main groups of the periodic system and of the transition metals such as for example lithium nitrite, sodium nitrite, potassium nitrite, magnesium nitrite, calcium nitrite, aluminium nitrite, iron nitrite or copper nitrite.

Preferred organic nitrites are nitrous acid esters of the formula $$E-O-N=O,$$

wherein
E represents a $C_1-C_{10}$-alkyl radical which is optionally substituted by OH, O-alkyl, O-acetyl or ONO.

The following organic nitrites may be mentioned as examples:

methyl nitrite, ethyl nitrite, n-propyl nitrite, i-propyl nitrite, n-butyl nitrite, i-butyl nitrite, s-butyl nitrite, n-pentyl nitrite, i-pentyl nitrite, all of the isomers of hexyl, heptyl and octyl nitrites, 2-methoxyethyl nitrite, 2-ethoxyethyl nitrite, 2-propoxyethyl nitrite, 2-butoxyethyl nitrite and 1-methoxyprop-2-yl nitrite, as well as nitrous acid mono- and diesters of 1,2-ethanediol, 1,2-propanediol, 1,3-propanediol, 1,4-butanediol, 1,5-pentanediol, 1,6-hexanediol, 2-methyl-1,3-propanediol, 2,2-dimethyl-1,3-propanediol, 2,2-diethyl-1,3-propanediol, 1-propyl-2-ethyl-1,3-propanediol, 1-propyl-2,2-dimethyl-1,3-propanediol, 2-ethyl-2-butyl-1,3-propanediol, diethylene glycol, di-1,2-propyleneglycol and triethylene glycol and further of the methyl, ethyl, propyl and butyl half-ethers of diethylene glycol, di-1,2-propylene glycol and triethylene glycol as well as nitrous acid esters of pentaerythritol and the alkyl ethers derived therefrom.

The preparation of triazatrimethine dyestuffs has hitherto been carried out by diazotisation of the aromatic or heterocyclic amines in mineral acid solution, addition of the diazonium salt solution to the solution of the coupling component and coupling by addition of acid-binding agents (compare, for example, DE-A 1 069 563).

In all cases, an inorganic or organic acid was hitherto employed for the diazotisation and had to be neutralised during the subsequent coupling. Inorganic salts are formed here. These inorganic salts enter the waste water during isolation of the dyestuff and represent pollution. When mixed with the dyestuff prepared, inorganic salts often influence the solubility in an adverse manner. To prepare stable dyestuff solutions, these salts must be removed by expensive processes, for example pressure permeation or reverse osmosis. All these disadvantages can be avoided by the new preparation process according to the invention.

The dyestuffs of the formula (I) according to the invention are particularly suitable for dyeing and printing naturally occurring and synthetic materials, in particular fibres of polyacrylonitrile, acid-modified polyesters and polyamides.

Dyeing can be carried out from a weakly acid liquor, the goods expediently being introduced into the dyebath at 40° to 60° C. and dyeing then being carried out at the boiling point. Dyeing can also be carried out under pressure at temperatures above 100° C. The dyestuffs furthermore can be added to spinning solutions for production of fibres containing polyacrylonitrile, or can also be applied to the non-stretched fibre.

Dyeings of the dyestuffs of the formula (I) according to the invention on materials of polyacrylonitrile or acid-modified polyester fibres or polyamide fibres are distinguished by very good fastness to light, wet processing, rubbing and sublimation and by a high affinity for the fibre.

Examples of compounds of the formula (IV) are:

2,5-diamino-1,3,4-thiadiazole, 2-amino-5-(di)methylamino-1,3,4-thiadiazole, 2-amino-5-(di)ethylamino-1,3,4-thiadiazole, 2-amino-5-(di)-n-propylamino-1,3,4-thiadiazole, 2-amino-5-(di)-i-propylamino-1,3,4-thiadiazole, 2-amino-5-(di)butylamino-1,3,4-thiadiazole, 2-amino-5-(di)phenylamino-1,3,4-thiadiazole, 2-amino-5-phenylmethylamino-1,3,4-thiadiazole, 2-amino-5-(di)benzylamino-1,3,4-thiadiazole, 2-amino-5-benzylmethylamino-1,3,4-thiadiazole, 2-amino-5-phenethylmethylamino-1,3,4-thiadiazole, 2-amino-5-morpholino-1,3,4-thiadiazole, 2-amino-5-piperidino-1,3,4-thiadiazole, 2-amino-5-pyrrolidino-1,3,4-thiadiazole, 2-amino-5-(di)cyclohexylamino-1,3,4-thiadiazole, 2-amino-5-cyclohexylmethylamino-1,3,4-thiadiazole, 2-amino-5-hydroxyethylmethylamino-1,3,4-thiadiazole, 2-amino-5-(di)hydroxyethylamino-1,3,4-thiadiazole, 2-amino-5-(di)hydroxypropylamino-1,3,4-thiadiazole, 2-amino-5-cyanoethylmethylamino-1,3,4-thiadiazole and 2-amino-5-biscyanoethylamino-1,3,4-thiadiazole.

Examples of quaternary salts of heterocyclic amines of the formula (V) which can be employed are:

2-amino-3-methylbenzothiazolium, 2-amino-3-ethylbenzothiazolium, 2-amino-3-methyl-6-methylbenzothiazolium, 2-amino-3-methyl-6-methoxybenzothiazolium, 2-amino-3-methyl-6-nitrobenzothiazolium, 2-amino-3-methyl-6-ethoxybenzothiazolium, 2-amino-3-methyl-1,3-thiazolium, 2-amino-3-methyl-5-methyl-1,3-thiazolium, 2-amino-3-methyl-5-ethyl-1,3-thiazolium, 2-amino-3-methyl-5-t-butyl-1,3-thiazolium, 2-amino-3-methyl-5-phenyl-1,3-thiazolium, 2-amino-3-methyl-4,5-dimethyl-1,3-thiazolium, 2-amino-3-methyl-4,5-diphenyl-1,3-thiazolium, 3-amino-1,4-dimethyl-1,2,4-triazolium, 3-amino-1,4-diethyl-1,2,4-triazolium, 3-amino-1,4-dimethyl-5-ethyl-1,2,4-triazolium, 3-amino-1,4-dimethyl-5-cyanoethyl-1,2,4-triazolium, 3-amino-1,4-dimethyl-5-butyl-1,2,4-triazolium, 3-amino-1,4-dimethyl-5-phenyl-1,2,4-triazolium, 3-amino-1,4-dimethyl-5-p-tolyl-1,2,4-triazolium, 2-amino-5-(di)methylamino-1,3,4-thiadiazolium, 2-amino-5-(di)ethylamino-1,3,4-thiadiazolium, 2-amino-5-(di)-n-propylamino-1,3,4-thiadiazolium, 2-amino-5-(di)-i-propylamino-1,3,4-thiadiazolium, 2-amino-5-(di)-n-butylamino-1,3,4-thiadiazolium, 2-amino-5-(di)phenylamino-1,3,4-thiadiazolium, 2-amino-5-phenylmethylamino-1,3,4-thiadiazolium, 2-amino-5-benzylmethylamino-1,3,4-thiadiazolium, 2-amino-5-phenethylmethylamino-1,3,4-thiadiazolium, 2-amino-5-morpholino-1,3,4-thiadiazolium, 2-amino-5-piperidino-1,3,4-thiadiazolium, 2-amino-5-pyrrolidino-1,3,4-thiadiazolium, 2-amino-5-(di)cyclohexylamino-1,3,4-thiadiazolium, 2-amino-5-cyclohexylmethylamino-1,3,4-thiadiazolium, 2-amino-5-(di)hydroxyethylmethylamino-1,3,4-thiadiazolium and 2-amino-5-cyanoethylmethylamino-1,3,4-thiadiazolium salts.

The quaternary salts of the formula (V) are obtainable, for example, by reaction of compounds of the formula (IV) with a quaternising agent, such as, for example, methyl iodide, ethyl iodide, propyl iodide, butyl iodide, dimethyl sulphate, ethylene oxide, propylene oxide, acrylonitrile, acrylamide, acrylic acid and its esters, α-halogenocarboxylic acids and their esters or epichlorohydrin.

The following examples are intended to illustrate the present invention.

EXAMPLE 1

20 g of 2-amino-5-diisopropylamino-1,3,4-thiadiazole, 27.6 g of 2-amino-3-methyl-1,3-benzothiazolium methosulphate, 12 g of isoamyl nitrite, 40 ml of water and 80 ml of methanol are combined in an autoclave, and the mixture is placed under a $CO_2$ pressure of 50 bar and heated to 40° C. It is stirred at this temperature under a constant pressure for 3 hours. The autoclave is then let down, the methanol is distilled off and the colour base of the formula

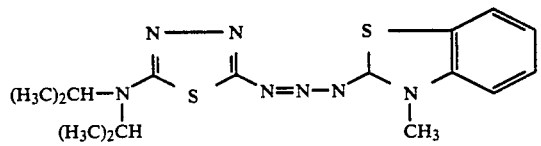

is discharged onto water and filtered off with suction. After drying, the yield is 28.5 g, melting point: 195°–198° C.

Methylation with dimethyl sulphate gives a cationic dyestuff which dyes polyacrylonitrile in a light-fast red shade and corresponds to the formula

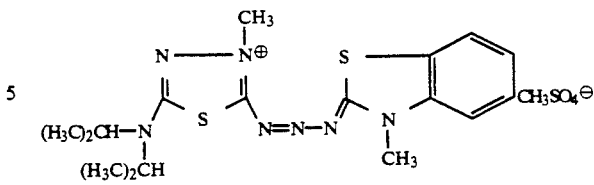

Similarly useful dyestuffs are obtained if, instead of 2-amino-3-methyl- 1,3-benzothiazolium methosulphate, the methylated quaternary salts of 3-aminotriazole, of 2-aminothiazole or of 2-amino-diisopropylamino- 1,3,4-thiadiazole are employed for the synthesis of the colour base.

The colour bases of the formula (II) listed in Table 1 which, after quaternisation, lead to the corresponding dyestuffs of the formula (I), which have the absorption wavelengths stated in Table 1, can be prepared analogously to Example 1.

TABLE 1

| Example | Structure | Quaternising agent | $R^2$ | $An^\ominus$ | $\lambda_{max}[nm]$ |
|---|---|---|---|---|---|
| 2 | benzothiazole-N(CH₃)-N=N-C(S)-N=N-C(B)(N-)... with N(CH₃)₂ | Dimethyl sulphate | $R^2 = CH_3$ | $CH_3SO_4^\ominus$ | 490 |
| 3 | (CH₃)N-N=N-C(S)-N=N-C(B) with N(CH₃)₂ | Dimethyl sulphate | $R^2 = CH_3$ | $CH_3SO_4^\ominus$ | 492 |
| 4 | benzothiazole with N(iPr)₂ | Dimethyl sulphate | $R^2 = CH_3$ | $CH_3SO_4^\ominus$ | 492 |
| 5 | benzothiazole with N(iPr)₂ | Acrylonitrile | $R^2 = CH_2CH_2CN$ | $Cl^\ominus$ | 465 |
| 6 | benzothiazole with N(iPr)₂ | Benzyl chloride | $R^2 = CH_2$–phenyl | $Cl^\ominus$ | 498 |
| 7 | 5-OCH₃-benzothiazole with N(iPr)₂ | Dimethyl sulphate | $R^2 = CH_3$ | $CH_3SO_4^\ominus$ | 505 |

TABLE 1-continued

| Example | B (structure) | Quaternising agent | R² group | An⊖ | λ_max [nm] |
|---|---|---|---|---|---|
| 8 | bis(isopropyl)amino-thiazole with N-methyl pyrazole | Dimethyl sulphate | R² = CH₃ | CH₃SO₄⊖ | 492 |
| 9 | N-methyl benzothiazole / phenylamino-thiazole (NH) | Dimethyl sulphate | R² = CH₃ | CH₃SO₄⊖ | 498 |
| 10 | N-methyl benzothiazole / N-methyl-phenylamino-thiazole | Dimethyl sulphate | R² = CH₃ | CH₃SO₄⊖ | 500 |
| 11 | bis(isopropyl)amino-thiazole / morpholino-thiazole | Dimethyl sulphate | R² = CH₃ | CH₃SO₄⊖ | 496 |
| 12 | bis-morpholino-thiazole | Dimethyl sulphate | R² = CH₃ | CH₃SO₄⊖ | 494 |

TABLE 1-continued

| Example | Structure | Quaternising agent | | An⊖ | λ_max[nm] |
|---|---|---|---|---|---|
| 13 | benzothiazole-N(CH₃)-C(=N-N=N-Z)-S-C(=N-N=N-Z)-N(CH₃)CH₂CH₂OH with benzothiazole containing CH₃ on N | Dimethyl sulphate | R² = CH₃ | CH₃SO₄⊖ | 496 |
| 14 | analogous with N(CH₂CH₂OH)₂ | Dimethyl sulphate | R² = CH₃ | CH₃SO₄⊖ | 496 |
| 15 | analogous with N(CH₃)CH₂CH₂CN | Dimethyl sulphate | R² = CH₃ | CH₃SO₄⊖ | 490 |
| 16 | analogous with N(CH₂CH₂CN)₂ | Dimethyl sulphate | R² = CH₃ | CH₃SO₄⊖ | 488 |

What is claimed is:

1. A triazatrimethine dyestuff of the formula (I)

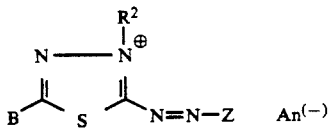  (I)

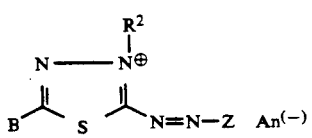  (I)

wherein

Z represents a radical of the formula

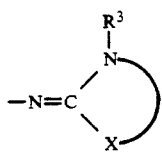

wherein $R^3$ represents hydrogen or an alkyl, alkenyl or aralkyl radical and

X represents the remaining members of a five-membered, optionally substituted and optionally fused partly unsaturated heterocyclic ring which contains one to three hereto atoms selected from the group consisting of oxygen, sulphur and nitrogen, B represents alkylmercapto, arylmercapto or a radical of the formula

wherein

R denotes hydrogen or an alkyl, alkenyl, acyl, cycloalkyl, aryl, aralkyl, amino, alkylamino, dialkylamino, arylamino, aralkylamino or heterocyclic radical and $R^1$ denotes hydrogen or an alkyl, alkenyl or aralkyl radical, or R and $R^1$ together with the nitrogen atom to which they are attached form a heterocyclic ring, $R_2$ represents hydrogen or an alkyl, alkenyl, alkinyl or aralkyl radical and $An^{(-)}$ represents an anion, and wherein the cyclic and acyclic radicals can contain non-ionic substituents and/or a carboxyl group.

2. Triazatrimethine dyestuff of claim 1, wherein

Z represents a radical of the formula

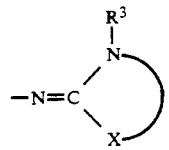

wherein $R^3$ represents hydrogen, or represents $C_1$–$C_8$-alkyl which is optionally substituted by hydroxyl, halogen, cyano, $C_1$–$C_4$-alkoxy, carboxyl, $C_1$–$C_4$-alkylamino, $C_1$–$C_4$-dialkylamino, $C_1$–$C_4$-alkoxycarbonyl or $C_1$–$C_4$-alkylsulphonyl, or represents $C_2$–$C_4$-alkenyl, or represents phenyl-$C_1$–$C_2$-alkyl, which is optionally substituted by halogen, cyano, $C_1$–$C_4$-alkyl or $C_1$–$C_4$-alkoxy and X represents the remaining members of a thiazoline, isothiazoline, benzothiazoline, 1,2,4-triazoline, 1,3,4-thiadiazoline, oxazoline, benzoxazoline, imidazoline, benzimidazoline, pyrazoline or benzopyrazoline ring, which is in each case optionally mono- or disubstituted by identical or different $C_1$–$C_8$-alkyl, which is optionally substituted by hydroxyl, halogen, cyano, $C_1$–$C_4$-alkoxy, carboxyl, $C_1$–$C_4$-alkylamino, $C_1$–$C_4$-dialkylamino, $C_1$–$C_4$-alkoxycarbonyl or $C_1$–$C_4$-alkylsulphonyl, or represents $C_2$–$C_4$-alkenyl, or represents phenyl-$C_1$–$C_2$-alkyl, which is optionally substituted by halogen, cyano, $C_1$–$C_4$-alkyl or $C_1$–$C_4$-alkoxy, B represents a radical of the formula

wherein

R represents hydrogen, or represents a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, or represents a $C_2$–$C_4$-alkenyl radical, a cyclohexyl radical which is optionally substituted by $C_1$–$C_4$-alkyl, or represents a phenyl, benzyl or phenylethyl radical which in each case is optionally substituted by halogen, $C_1$–$C_4$-alkyl or $C_1$–$C_4$-alkoxy, or represents a $C_1$–$C_4$-alkyloxycarbonyl, mono- or di-$C_1$–$C_4$-alkylaminocarbonyl, aminocarbonyl, mono- or di-$C_1$–$C_4$-alkylaminosulphonyl, amino, $C_1$–$C_4$-alkylamino or $C_1$–$C_4$-dialkylamino radical, or represents a phenylamino or benzylamino radical which in each case is optionally substituted by $C_1$–$C_4$-alkyl or $C_1$–$C_4$-alkoxy and $R^1$ represents hydrogen, a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, or represents a $C_2$–$C_4$-alkenyl radical or represents a phenyl, benzyl or phenylethyl radical which in each case is optionally substituted by halogen, $C_1$–$C_4$-alkyl or $C_1$–$C_4$-alkoxy, and $R^2$ represents hydrogen, a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, or represents a $C_2$–$C_4$-alkenyl radical or represents a benzyl or phenylethyl radical which in each case is optionally substituted by halogen, $C_1$–$C_4$-alkyl or $C_1$–$C_4$-alkoxy.

3. Dyestuff of claim 1, wherein

Z represents a radical of the formula

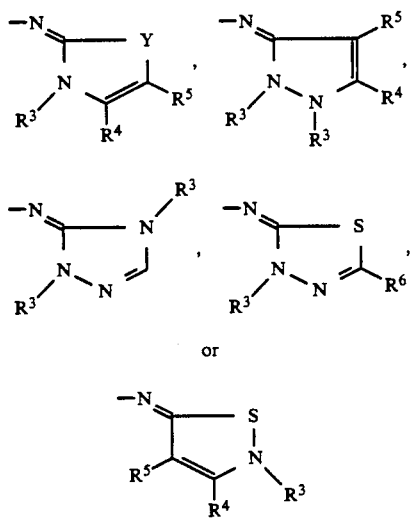

or

wherein
Y represents —S—, —O— or $$-\underset{R^3}{N}-,$$

wherein $R^3$ has the abovementioned meaning, and if two substituents $R^3$ occur, these can be identical or different, $R^4$ and $R^5$ either represent hydrogen, or together represent the remaining members of a fused-on benzene ring, and $R^6$ represents $C_1$-$C_4$-alkylamino, $C_6$-$C_{10}$-dialkylamino, $C_6$-$C_{10}$-arylamino, $C_6$-$C_{10}$-diarylamino, piperazino, pyrrolidino, $C_1$-$C_4$-alkylmercapto or $C_6$-$C_{10}$-arylmercapto, B represents a radical of the formula $$\underset{R^1}{\overset{R}{\diagdown}}N-$$

wherein

R represents hydrogen, a $C_1$-$C_4$-alkyl radical which is optionally substituted by hydroxyl, halogen, cyano, $C_1$-$C_4$-alkoxy, carbonyl, aminocarbonyl or $C_1$-$C_4$-alkoxycarbonyl, or represents a phenyl, benzyl or phenylethyl radical which in each case is optionally substituted by halogen, $C_1$-$C_4$-alkyl $C_1$-$C_4$-alkoxy and $R^1$ represents a $C_1$-$C_4$-alkyl radical which is optionally substituted by hydroxyl, halogen, cyano, $C_1$-$C_4$-alkoxy, carboxyl, aminocarbonyl or $C_1$-$C_4$-alkoxycarbonyl, or represents a benzyl or phenylethyl radical which in each case is optionally substituted by halogen, $C_1$-$C_4$-alkyl or $C_1$-$C_4$-alkoxy, and $R^2$ represents hydrogen, a $C_1$-$C_8$-alkyl radical which is optionally substituted by hydroxyl, halogen, cyano, $C_1$-$C_4$-alkoxy, carboxyl, aminocarbonyl or $C_1$-$C_4$-alkoxycarbonyl or represents a benzyl or phenylethyl radical which in each case is optionally substituted by halogen, $C_1$-$C_4$-alkyl or $C_1$-$C_4$-alkoxy.

4. Dyestuff of the formula

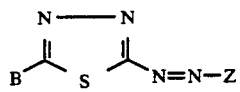

(II)

wherein

Z represents a radical of the formula

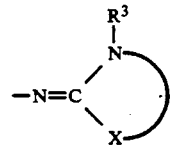

wherein $R^3$ represents hydrogen or an alkyl, alkenyl or aralkyl radical and

X represents the remaining members of a five-membered, optionally substituted and optionally fused partly unsaturated heterocyclic ring which contains one to three hetero atoms selected from the group consisting of oxygen, sulphur and nitrogen, B represents alkylmercapto, arylmercapto or a radical of the formula

wherein

R denotes hydrogen or an alkyl, alkenyl, acyl, cycloalkyl, aryl, aralkyl, amino, alkylamino, dialkylamino, arylamino, aralkylamino or heterocyclic radical and $R^1$ denotes hydrogen or an alkyl, alkenyl or aralkyl radical, or R and $R^1$ together with the nitrogen atom to which they are attached form a heterocyclic ring, $R^2$ represents hydrogen or an alkyl, alkenyl, alkinyl or aralkyl radical and $An^{(-)}$ represents an anion.

5. Dyestuff of claim 4, wherein

Z represents a radical of the formula

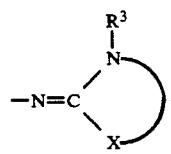

wherein $R^3$ represents hydrogen, $C_1$-$C_8$-alkyl which is optionally substituted by hydroxyl, halogen, cyano, $C_1$-$C_4$-alkoxy, carboxyl, $C_1$-$C_4$-alkylamino, $C_1$-$C_4$-dialkylamino, $C_1$-$C_4$-alkoxycarbonyl or $C_1$-$C_4$-alkylsulphonyl, or represents $C_2$-$C_4$-alkenyl, or represents phenyl-$C_1$-$C_2$-alkyl, which is optionally substituted by halogen, cyano, $C_1$-$C_4$-alkyl or $C_1$-$C_4$-alkoxy and X represents the remaining members of a thiazoline, isothiazoline, benzothiazoline, 1,2,4-triazoline, 1,3,4-thiadiazoline, oxazoline, benzoxazoline, imidazoline, benzimidazoline, pyrazoline or benzopyrazoline ring, which is in each case optionally mono- or disubstituted by identical or different $C_1$–$C_8$-alkyl, which is optionally substituted by hydroxyl, halogen, cyano, $C_1$–$C_4$-alkoxy, carboxyl, $C_1$–$C_4$-alkylamino, $C_1$–$C_4$-dialkylamino, $C_1$–$C_4$-alkoxycarbonyl or $C_1$–$C_4$-alkylsulphonyl, or represents $C_2$–$C_4$-alkenyl, or represents phenyl-$C_1$–$C_2$-alkyl, which is optionally substituted by halogen, cyano, $C_1$–$C_4$-alkyl or $C_1$–$C_4$-alkoxy, B represents a radical of the formula

wherein

R represents hydrogen, a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, or represents a $C_2$–$C_4$-alkenyl radical, a cyclohexyl radical which is optionally substituted by $C_1$–$C_4$-alkyl, or represents a phenyl, benzyl or phenylethyl radical which in each case is optionally substituted by halogen, $C_1$–$C_4$-alkyl or $C_1$–$C_4$-alkoxy, or represents a $C_1$–$C_4$-alkyloxycarbonyl, mono- or di-$C_1$–$C_4$-alkylaminocarbonyl, aminocarbonyl, mono- or di-$C_1$–$C_4$-alkylaminosulphonyl, amino, $C_1$–$C_4$-alkylamino or di-($C_1$–$C_4$-alkyl)-amino radical, or a phenylamino or benzylamino radical which is optionally substituted by $C_1$–$C_4$-alkyl or $C_1$–$C_4$-alkoxy and $R^1$ represents hydrogen, a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, or represents a $C_2$14 $C_4$-alkenyl radical or represents a phenyl, benzyl, or phenylethyl radical which in each case is optionally substituted by halogen, $C_1$–$C_4$-alkyl or $C_1$–$C_4$-alkoxy, and $R^2$ represents hydrogen, a $C_1$–$C_8$-alkyl radical which is optionally substituted by hydroxyl, halogen, cyano, $C_1$–$C_4$-alkoxy, carboxyl, aminocarbonyl or $C_1$–$C_4$-alkoxycarbonyl, or represents a $C_2$–$C_4$-alkenyl radical or represents a benzyl or phenylethyl radical which in each case is optionally substituted by halogen, $C_1$–$C_4$-alkyl or $C_1$–$C_4$-alkoxy.

6. A process for dyeing and printing naturally occurring and synthetic matrials by applying thereto at least one dyestuff of the formula (I) of claim 1.

7. A process for dyeing and printing naturally occurring and synthetic materials by applying thereto at least one dyestuff of the formula (II) of claim 4 is employed.

8. A process for bulk dyeing of plastics by applying thereto at least one dyestuff of the formula (II) of claim 4.

9. A process according to claim 6 wherein the naturally occuring and synthetic materials are fibres of polyacrylonitrile, acid-modified polyesters and polyamides.

10. A process according to claim 7 wherein the naturally occuring and synthetic materials are fibres and fabrics of materials which can be dyed with nonionic dyestuffs.

11. A dyestuff mixture which contains at least two dyestuffs of the formula (I) of claim 1.

12. A dyestuff mixture which contains at least two dyestuffs of the formula (II) of claim 4.

* * * * *

UNITED STATES PATENT AND TRADEMARK OFFICE
CERTIFICATE OF CORRECTION

PATENT NO : 5,328,993
DATED : July 12, 1994
INVENTOR(S): Hauke Furstenwerth, et al.

It is certified that error appears in the above-identified patent and that said Letters Patent is hereby corrected as shown below:

Column 19, lines 36 and 37      cancel "$C_6$-$C_{10}$-dialkylamino" and substitute --$C_1$-$C_4$-dialkylamino--

Column 22, line 2,      after "$C_2$" cancel "14"

Column 22, line 19,      cancel "is employed"

Signed and Sealed this

Twenty-ninth Day of June, 1999

*Attest:*

Q. TODD DICKINSON

*Attesting Officer*      *Acting Commissioner of Patents and Trademarks*